United States Patent
Berlin et al.

(10) Patent No.: US 7,183,336 B2
(45) Date of Patent: Feb. 27, 2007

(54) IRRADIATED ABSORBENT MATERIALS

(75) Inventors: Phillip Berlin, Trabucco Canyon, CA (US); Mark Sinkinson, Laguna Hills, CA (US)

(73) Assignee: Super Absorbent Company, Irvine, CA (US)

( * ) Notice: Subject to any disclaimer, the term of this patent is extended or adjusted under 35 U.S.C. 154(b) by 307 days.

(21) Appl. No.: 10/502,819

(22) PCT Filed: Jul. 30, 2003

(86) PCT No.: PCT/US03/24821

§ 371 (c)(1),
(2), (4) Date: Aug. 26, 2004

(87) PCT Pub. No.: WO2004/030703

PCT Pub. Date: Apr. 15, 2004

(65) Prior Publication Data
US 2005/0020713 A1    Jan. 27, 2005

Related U.S. Application Data

(60) Provisional application No. 60/415,970, filed on Oct. 2, 2002.

(51) Int. Cl.
*C08F 2/46* (2006.01)

(52) U.S. Cl. .............. 522/88; 522/1; 522/87; 522/89; 204/157.6; 204/157.61; 204/157.63; 502/401; 502/403; 502/404; 502/400; 502/526; 428/402; 428/404; 526/200; 424/443; 604/358; 604/367; 604/374

(58) Field of Classification Search .................. 522/86, 522/84, 85, 87, 88, 79, 1, 2, 96, 104; 204/157.6, 204/157.61, 157.62; 502/401, 403, 404, 502/522, 510, 526; 428/402, 404; 526/200; 424/443; 604/358, 367, 374
See application file for complete search history.

(56) References Cited

U.S. PATENT DOCUMENTS

| | | | |
|---|---|---|---|
| 3,935,099 A | | 1/1976 | Weaver et al. |
| 3,981,100 A | | 9/1976 | Weaver et al. |
| 3,985,616 A | | 10/1976 | Weaver et al. |
| 3,997,484 A | | 12/1976 | Weaver et al. |
| 4,340,057 A | * | 7/1982 | Bloch et al. ............. 604/358 |
| 5,470,964 A | * | 11/1995 | Qin ............................ 536/20 |
| 5,863,958 A | | 1/1999 | Dyer et al. |
| 6,011,196 A | * | 1/2000 | Wang et al. .............. 604/368 |
| 6,239,230 B1 | * | 5/2001 | Eckert et al. ............ 525/329.9 |
| 6,293,935 B1 | | 9/2001 | Kimura et al. |
| 6,391,451 B1 | * | 5/2002 | Mitchell et al. ............ 428/402 |
| 6,439,492 B1 | | 8/2002 | Leiggi |
| 2004/0186239 A1 | * | 9/2004 | Qin et al. ................. 525/327.4 |

* cited by examiner

Primary Examiner—Sanza L. McClendon
(74) Attorney, Agent, or Firm—Rutan & Tucker, LLP

(57) ABSTRACT

Polymer particles are irradiated with radiation from a high energy source to increase the water or other fluid absorbency of the particles. Products manufactured using the activated particles include protective undergarments, bandages, kitty litter, and spill clean up materials.

20 Claims, 1 Drawing Sheet

IRRADIATED ABSORBENT MATERIALS

This application claims the benefit of U.S. provisional application No. 60/415,970, filed Oct. 2, 2002 incorporated herein by reference in its entirety.

FIELD OF THE INVENTION

The field of the invention is absorbent materials.

BACKGROUND OF THE INVENTION

Materials that absorb up to about 20 times their own weight are well known. U.S. Pat. No. 6,293,935 issued to Kimura et al. (Sep. 25, 2001) teach the use of a wide range of polymeric materials, including starch, crosslinked carboxymethylated cellulose, and polyacrylic acid. Some of the most absorbent materials ever discovered are alkali saponified gelatinized-starch-polyacrylonitrile graft polymers. Examples are discussed in U.S. Pat. No. 3,985,616. (Oct. 12, 1976), U.S. Pat. No. 3,935,099 (Jan. 27, 1976), U.S. Pat. No. 3,981,100 (Sep. 21, 1976), and U.S. Pat. No. 3.997,484 (Dec. 14, 1976), all issued to Weaver et al. Although some of those patents assert that the starch-containing polymer compositions may be able to absorb amounts of water equaling up to more than 1000 times their own weight, such statements in the prior art did not were not borne out in practice. To date, the highest absorbance of fluid has only been about 150 times wt/wt.

Since highly absorbent materials provide increased efficiency and convenience, and reduce cost and environmental waste, there are continuing efforts to provide even higher absorbencies. U.S. Pat. No. 6,439,492 issued to Leiggi (Aug. 27, 2002) teaches an absorbent pad comprising a main enclosure having an absorbing element used to absorb fluids dropped by motor vehicles. Given the amount of fluid that may be dropped from an automobile, it would be helpful to provide greater absorbencies than that taught by Leiggi.

One method of increasing absorbency is to provide materials with numerous activated double bonds. U.S. Pat. No. 5,863,958 issued to Dyer et al. (Jan. 26, 1999). Dyer et al. teach polymers made from 1,3,7-octatriene or like conjugated polyenes, and a crosslinking agent having at least 2 activated double bonds. A preferred product using that technology is ethylene glycol dimethacrylate. Dyer et al. teach that such polymers can be used to make absorbent foams that are useful in articles such as diapers, as well as latexes that are useful as binders and adhesives.

There is, however, no recognized method of activating polymers in general, so that they can achieve very high absorbencies of 250 wt/wt or more.

SUMMARY OF THE INVENTION

The present invention provides broadly applicable methods and apparatus for activating polymers to increase hydrophilicity and absorption.

Of special interest are methods of activating starch-related polymer products, and the compositions and products themselves. As used herein the term "polymer products" means polymers having any non-trivial number of activated individual starch particles or molecules. In preferred embodiments, a batch of activated starch has at least 100 g of starch particles.

According to a preferred method, non-activated polymer particles are subjected to a high energy source under conditions that produce a mosaic ionic pattern on the surface of the particles. Such surface modifications increase the particles' ability to absorb water and other liquids, and thereby also increase the hydrophilicity of the particles. While not wishing to be limited by any particular theory or mechanism of action, the inventors currently contemplate that the energy utilized is sufficient to open chemical bonds on the order of at least 1 angstrom on the surface of the particles.

Plasmas are the preferred high energy source, although other high energy sources such as UV sources or Lasers can also be used.

Various objects, features, aspects and advantages of the present invention will become more apparent from the following detailed description of preferred embodiments of the invention, along with the accompanying drawings in which like numerals represent like components.

DETAILED DESCRIPTION

Figure 1:
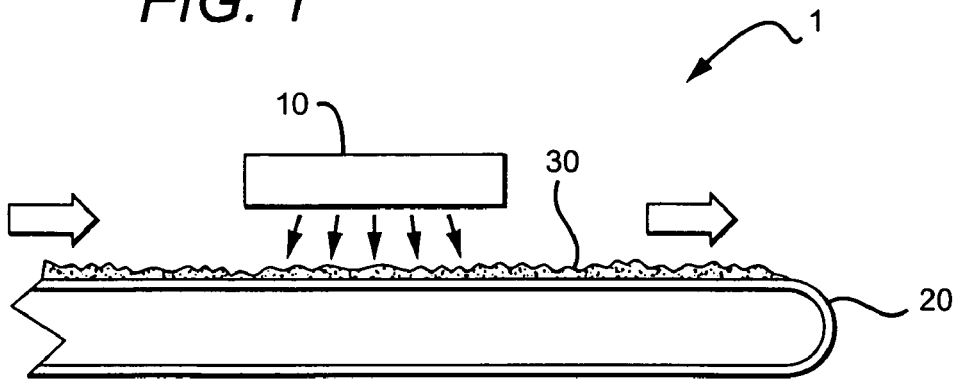
FIG. 1 is a schematic of irradiation of polymer particles by an energy source.

In FIG. 1 a conveyor belt 20 is passing a load of polymer particles 30 past a high energy source 10 (such as a plasma or UV tube).

In more general terms, any suitable polymer particles are activated using radiation from any suitable high energy source. This is preferably done under conditions sufficient to open multiple covalent bonds on at least some surfaces by a length of at least one angstrom, and sufficient to increase the water absorbency of the activated (irradiated) polymer by at least 20% on a wt/wt basis relative to the non-activated (non-irradiated) polymer. Of course, in preferred embodiments, irradiation of the polymer particles increases their water absorbency by at least 50%, and even higher.

A wide range of polymers are contemplated for use in the invention, including glucosidics, acrylics, acrylic acid copolymers, polyacrylamide/acrylic acid copolymers, starch, carboxymethyl cellulose, carboxymethyl cellulose gum and sulphonated cellulose. Preferred polymers for irradiation are starches. Polymers can be employed in the invention whether or not they have native surface ionic groups. U.S. Pat. No. 5,252,340 to Honeycutt (October 1993) and U.S. Pat. No. 4,865,640 to Avera (September 1989) describes many of the suitable starches. These and all other patents identified herein are incorporated by reference. Polymers are preferably dried before irradiation to increase absorption of the radiation, and then re-suspended in solution if desired after irradiation to provide a more homogeneous solution. Polymerization can be accomplished before, during, or following irradiation.

Since the increase in absorbance is thought to involve surface effects, the polymer is preferably rendered into particles, having average molecular weight of 90,000 to 700,000. Preferred particles have mean diameter (assuming the particle were spherical) of no more than about 5 mm. For some applications, smaller particles are preferred, such as from 150 to 1000 microns. Unless otherwise noted, all ranges herein should be interpreted as being inclusive of the endpoints. On the other hand, it is helpful in some instances for the particles to be relatively larger, having diameters of greater than 5 mm. Methods of preparation and measurement can be found in U.S. patent application, 20020098983.

Plasmas are currently the preferred high energy sources because plasmas provide a very high level of high energy radiation at a relatively low cost. Many different types of plasmas can be used, including radio-frequency inductive and capacitive discharge plasmas. Cold type plasma devices are especially preferred those in which the ionized atoms are cooler than 10,000° K. The gas in a plasma generator may be any gas including for example, argon, oxygen, air, other noble gases and mixtures of the above gases with small quantities of water vapor to the primary plasma gas. The gas is typically held at low pressure, defined herein to mean less than 100 Torr. The plasma generator can even be "open", with a working pressure up to 1 atm. The plasma reactor is preferably made of stainless steel to reduce corrosion effects, although any sufficiently strong and resistant material may be used. Examples of other materials that may be used for reactor include titanium, tantalum, quartz, stainless steel coated with titanium, molybdenum, anodized aluminum, iridium, platinum, etc. For RF plasmas, a voltage of approximately 500–10,000 V can be applied to the RF torch, which is electrically grounded for safety and other reason. Preferred RF plasmas have a basic frequency of between 0.44 MHz and 40.68 MHz, and a power between 100 watts (W) to 100 KW. Other contemplated high energy sources include LASER sources, UV sources, and other radiation sources.

The polymer particles can be carried past the plasma or other radiation source at any suitable rate. This can be readily determined by experiment. Using the RF plasmas described above, it is contemplated that starch can be effectively irradiated at a rate of approximately 1 pound to about 200 pounds of particles per hour, especially if the particles are in direct contact with the plasma.

Using methods and apparatus described herein, starch or other polymer particles can be irradiated to provide fluid absorbencies or at least 250 times on a wt/wt basis. By adjusting the power and residence time, it is contemplated that activated materials may be able to absorb fluids at up to 400 or even 500 times their own weight.

Figure 2:
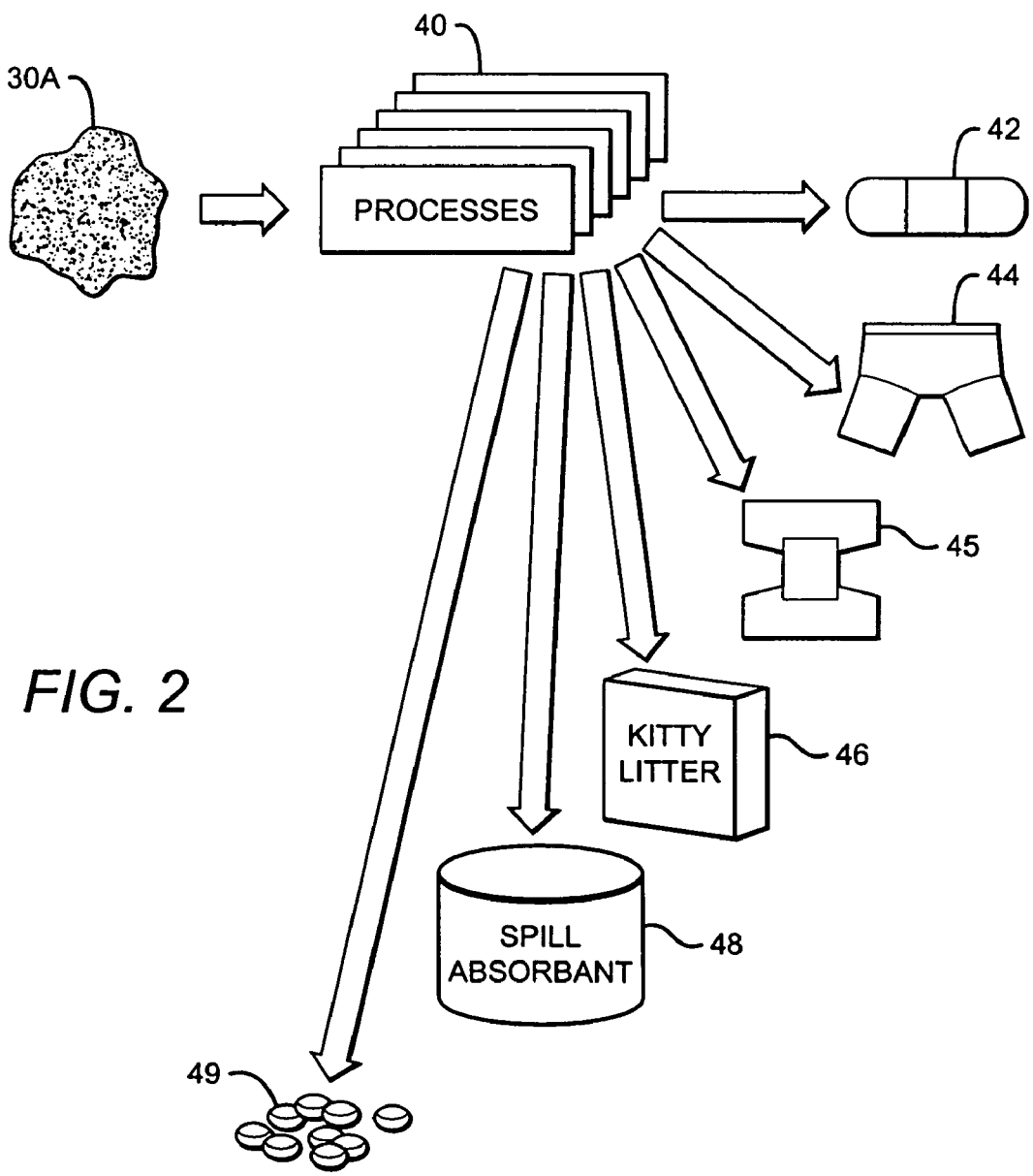
FIG. 2 is a schematic of production of various articles of manufacture that include irradiated polymer particles.

In FIG. 2, the irradiated particles 30A are being alternatively processed by processes 40 into different articles of manufacture, a band-aid 42, underpants 44, diaper 45, kitty litter 46, industrial spill absorbent 48, and pills 49 to be ingested.

In more general terms, activated polymers have a wide range of applications. Once class of applications includes containing effluent from animals and humans. This includes protective undergarments such as diapers and feminine hygiene products, and also bandages for wounds, toilet tissue, kitty litter, and so forth. Another class of products includes bags or other packages of spill cleanup materials, which may, for example, be used for example in containing and cleaning up automotive or other oil spills. These products should work much better in those applications that kitty litter, sawdust or sand.

Activated starch products may also be used in pharmaceutical applications. For example, activated products may be used as a drug delivery vehicle. Any particle that is injected intravenously into the human body must generally be less than 1 micron in diameter. Subjecting larger particles to a high-energy source typically breaks the particles down to sizes within the sub-micron range. Thus, in preferred embodiments, non-activated starch products may be subjected to plasma, which would create a porous surface on the particles. Those porous surfaces would then be capable of absorbing large amounts of pharmaceutical drug compounds. The "new" starch particle (the activated starch particle incorporating a pharmaceutical compound) can then be injected intravenously into a patient, or can be formulated for ingestion by a patient. Once in the body, the starch will likely be digested or dissolved, thus exposing the pharmaceutical compound. Another example includes ingesting or injecting activated starch or other particles into a patient's body to absorb toxins or other undesirable fluids.

Activated polymers may also be placed in soil to soak up excess moisture, and retain it for a period of time. Other contemplated products include activated polymers that contain chemical fertilizers, insecticides, anti-microbial agents, and so forth.

Activated products may also be employed in chemical reactions to absorb specific reactants or products. For example, a contemplated application in laboratories and in the chemical industry is using the activated particles in an ion exchange column. Polymers in paper and paper pulp may also be activated as described herein.

Thus, specific embodiments and applications of activated polymers have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

What is claimed is:

1. An article of manufacture created by the process of irradiating polymer particles with radiation from a high energy source under conditions that open multiple covalent bonds on at least some surfaces of at least some of the particles by a length of at least one angstrom such that the water absorbency of the polymer is thereby increased by at least 20% on a wt/w basis, when compared to the same non-irradiated polymer.

2. The article of claim 1, wherein the polymer comprises a starch.

3. The article of claim 1, wherein the particles have an average mean diameter of no more than 5 mm.

4. The article of claim 1, wherein the particles have an average mean diameter of more than 5 mm.

5. The article of claim 1, wherein the high energy source comprises a plasma.

6. The article of claim 5, wherein the plasma comprises an inductive plasma.

7. The article of claim 5, wherein the plasma comprises a capacitive plasma.

8. The article of claim 5, wherein the plasma comprises combination of inductive and capacitive plasmas.

9. The article of claim 5, wherein the plasma comprises an argon plasma.

10. The article of claim 5 wherein the plasma comprises RF plasma.

11. A protective undergarment comprising the irradiated particles of claim 1.

12. A bandage comprising the irradiated particles of claim 1.

13. A kitty litter comprising the irradiated particles of claim 1.

14. A package of irradiated particles of claim 1, labeled for use as spill clean up materials.

15. A drug delivery vehicle comprising the irradiated particles of claim 1.

16. A process of increasing the water absorbency of a polymer, comprising:
providing the polymer in particle form;
subjecting the particles to a plasma under conditions that opens multiple covalent bonds on at least some surfaces of at least some of the particles by a length of at least one angstrom sufficient to increase the water absorbency of the particles by at least 20% when compared to the same non-irradiated polymer.

17. The process of claim 16 wherein the polymer comprises starch.

18. The article of claim 16, wherein the particles have an average mean diameter of no more than 5 mm.

19. The article of claim 16, wherein the particles have an average mean diameter of more than 5 mm.

20. The article of claim 16, wherein the polymer comprises a cellulose.

* * * * *